United States Patent
Knuebel et al.

(10) Patent No.: US 10,955,344 B2
(45) Date of Patent: Mar. 23, 2021

(54) METHOD AND DEVICE FOR DETERMINING A DEGREE OF DAMAGE TO HAIR

(71) Applicant: Henkel AG & Co. KGaA, Duesseldorf (DE)

(72) Inventors: Georg Knuebel, Duesseldorf (DE); Antje Gebert-Schwarzwaelder, Neuss (DE); Annika Koenen, Grevenbroich (DE); Astrid Kroos, Monheim (DE); Melanie Moch, Dormagen (DE); Wilfried Howorka, Duesseldorf (DE)

(73) Assignee: Henkel AG & Co. KGaA, Duesseldorf (DE)

( * ) Notice: Subject to any disclaimer, the term of this patent is extended or adjusted under 35 U.S.C. 154(b) by 68 days.

(21) Appl. No.: 16/301,789

(22) PCT Filed: May 5, 2017

(86) PCT No.: PCT/EP2017/060758
§ 371 (c)(1),
(2) Date: Nov. 15, 2018

(87) PCT Pub. No.: WO2017/198479
PCT Pub. Date: Nov. 23, 2017

(65) Prior Publication Data
US 2019/0285546 A1    Sep. 19, 2019

(30) Foreign Application Priority Data

May 19, 2016  (DE) .................... 10 2016 208 631.6

(51) Int. Cl.
*G01N 21/64* (2006.01)
*G01N 21/91* (2006.01)
(Continued)

(52) U.S. Cl.
CPC ....... *G01N 21/6428* (2013.01); *A61B 5/0071* (2013.01); *G01N 21/91* (2013.01);
(Continued)

(58) Field of Classification Search
CPC .... G01N 21/64; G01N 21/91; G01N 21/6428; G01N 21/88; G01N 33/483; G01N 33/4833; A61B 5/448
(Continued)

(56) References Cited

U.S. PATENT DOCUMENTS

2008/0161661 A1    7/2008    Gizewski
2011/0155161 A1    6/2011    Samain
(Continued)

FOREIGN PATENT DOCUMENTS

JP    H09127105    *    5/1997
JP    H09127105 A         5/1997

OTHER PUBLICATIONS

Ehlers et al.: "Multiphoton Fluorescence Lifetime Imaging of Human Hair", Microscopy Research and Technique, Feb. 2007, pp. 154-161, XP055638624.
(Continued)

*Primary Examiner* — Jurie Yun
(74) *Attorney, Agent, or Firm* — Lorenz & Kopf, LLP (57) ABSTRACT

A method for determining a degree of damage to hair is provided in the form of various embodiments. Said method can comprise the following steps: during the exposure of a hair sample to UV light (for example by employing a UV-LED), detecting fluorescence light emitted by the hair sample, determining a fluorescence intensity by employing the detected light, and determining the degree of damage to the hair using said fluorescence intensity.

20 Claims, 6 Drawing Sheets

(51) Int. Cl.
　　　*G01N 33/483*　　(2006.01)
　　　*A61B 5/00*　　　(2006.01)
(52) U.S. Cl.
　　　CPC .......... *G01N 33/4833* (2013.01); *A61B 5/448* (2013.01); *G01N 2021/6495* (2013.01); *G01N 2201/062* (2013.01); *G01N 2201/12746* (2013.01)
(58) Field of Classification Search
　　　USPC .................... 250/459.1, 458.1, 461.1, 461.2
　　　See application file for complete search history.

(56) References Cited

U.S. PATENT DOCUMENTS

| | | |
|---|---|---|
| 2015/0148684 A1 | 5/2015 | Baym et al. |
| 2015/0223749 A1 | 8/2015 | Park et al. |

OTHER PUBLICATIONS

Silva et al.: "Rhodamine B diffusion in hair as a probe for structural integrity", Colloids and Surfaces B: Biointerfaces 40, 2005, pp. 19-24, XP027803318.
Tate et al.: "Quantification and prevention of hair damage", J. Soc. Cosmet. Chem., 44, pp. 347-371, Nov./Dec. 1993, XP055513866.
EPO, International Search Report and Written Opinion issued in International Application No. PCT/EP2017/060758 dated Jul. 7, 2017.
XP009144064, Sandhu S. S. et al.: "A sensitive fluorescence technique using dansyl chloride to assess hair damage", Journal of the Society Cosmetic Chem., vol. 40, No. 5, (Sep. 10, 1989), pp. 289-296.

\* cited by examiner

METHOD AND DEVICE FOR DETERMINING A DEGREE OF DAMAGE TO HAIR

CROSS-REFERENCE TO RELATED APPLICATION

This application is a U.S. National-Stage entry under 35 U.S.C. § 371 based on International Application No PCT/EP2017/060758, filed May 5, 2017 which was published under PCT Article 21(2) and which claims priority to German Application No. 10 2016 208 631.6, filed May 19, 2016, which are all hereby incorporated in their entirety by reference.

TECHNICAL FIELD

The present disclosure relates to a method and device for determining a degree of damage to hair, and to methods for determining a user-specific hair treatment product.

BACKGROUND

When treating hair using cosmetic products, an effect of the product, for example the intensity of a colouring, may be heavily dependent on the degree of damage of the hair.

Thus, it may be of great importance to determine the damage to hair.

Hair can be damaged by natural or artificially induced processes. The most notable type of damage may be oxidative damage.

The natural processes for example can have a combined (for example simultaneous) effect on UV light and oxygen ($O_2$) on the hair.

The artificially induced processes for example can include a use of hair dyes (also referred to as colorants), bleaching and/or the generation of permanent waves.

Besides the desired cosmetic effects, for example a lightening of the hair, the hair can also be heavily damaged, for example if oxidising agents are used.

The damage process can be brought about by an oxidation of amino acids, for example an oxidation of the amino acids cystine and cysteine, which occur very often in the hair, into cysteic acid. Cystine can form intermolecular disulphide bridges (also referred to as S bridges) in the hair, such that cystine is extremely important for the mechanical stability of the hair.

The oxidation of these bridges to form cysteic acid can destroy the mechanical stability of the hair and can even lead to complete hair breakage in the case of repeated use. However, properties of the hair that previously could be perceived, for example felt, macroscopically, for example a surface roughness, can also be negatively influenced. Results of cosmetic treatments, in particular of damaging procedures, can be massively changed already in an early stage of damage compared to a result achieved with undamaged hair.

The described mechanism of damage makes it possible to precisely determine the degree of the most notable damage, specifically the oxidative damage, by determining the content of cysteic acid.

In an academic and industrial field, a large number of physical and chemical analytical methods may be available to a researcher or developer in order to determine a degree of damage, for example in order to quantitatively determine a degree of oxidative damage.

Chromatography methods are usually used in this case, for example high-performance liquid chromatography (HPLC) based on complex hydrolysis.

Undamaged hair may typically have a cysteic acid content in the range from approximately 0.5% to approximately 1% (based on weight). If there is damage, for example as a result of repeated ultra-bleaching and/or other mechanisms of damage, the cysteic content may be increased to more than about 15% (by weight).

However, all of these chromatography methods are complicated and require a costly equipment set-up, such that they are not available to an end consumer.

Damaging cosmetic treatments, for example applications of heat, permanent waving or oxidative procedures, such as bleaching, and many others, are typically performed on the end consumer in the private field or in the field of commercial services. Although the performance of a further damaging procedure on hair that is already damaged may lead to catastrophic results, going as far as complete hair breakage, there was not previously any possibility within this scope to determine the degree of prior damage of the hair, for example quantitatively.

BRIEF SUMMARY

In an exemplary embodiment, a method for determining a degree of damage to hair is provided. The method includes exposing a hair sample of the hair to UV light and detecting light emitted by the hair sample to define detected light. A fluorescence intensity on a basis of the detected light is determined. A degree of damage to the hair using the fluorescence intensity of the hair sample is determined.

In another exemplary embodiment, a device for determining a degree of damage to hair is provided. The device includes a UV lamp configured for exposing a hair sample of the hair to UV light. A device is configured for detecting fluorescence light that is emitted by the hair sample to define detected light. A data processing device is configured for determining a fluorescence intensity on a basis of the detected light and for determining a degree of damage of the hair using the fluorescence intensity.

DETAILED DESCRIPTION

The following detailed description is merely exemplary in nature and is not intended to limit the disclosure or the application and uses of the subject matter as described herein. Furthermore, there is no intention to be bound by any theory presented in the preceding background or the following detailed description.

In the following detailed description, reference is made to the accompanying drawings, which form part of the present application and which, by way of illustration, shows specific embodiments in which the present disclosure can be implemented. It shall be understood that other embodiments may be used and structural or logical modifications may be made, without departing from the scope of protection of the present disclosure. It shall be understood that the features of the various exemplary embodiments described herein can be combined with one another, unless stated otherwise. The following detailed description therefore should not be understood to be limiting. The scope of protection of the present disclosure is defined by the appended claims.

In the present description the terms "predictive analytics", "big data" and "data mining" are used synonymously.

A number of fluorescent dyes are absorbed more heavily by oxidatively damaged hair than by undamaged hair. Reasons for this may be a high hydrophilicity of a hair surface following oxidative damage, in contrast to a pronounced hydrophobicity of undamaged hair.

In various exemplary embodiments this property is used to provide a method for determining a degree of damage to hair by a quantification, for example expressed as a content of cysteic acid, of a fluorescence intensity of the (damaged) hair surface.

In various exemplary embodiments damaged hair demonstrates inherent fluorescence, which is used to provide a method for determining a degree of damage to hair by way of a quantification, for example expressed as a content of cysteic acid, of a fluorescence intensity of the (damaged) hair surface.

In various exemplary embodiments suitable mathematical models based on predictive analytics can be used for the quantification.

In various exemplary embodiments an easy-to-use method is provided, which enables a precise determination of a degree of oxidative damage to hair with the aid of fluorescence detection and methods based on predictive analytics.

In various exemplary embodiments the method, on account of its simple experimental practicability, may be suitable for execution with use of a mobile data processing device. Here, a smartphone or a tablet or laptop can be used as mobile data processing device, for example.

In various exemplary embodiments a method may be provided which makes it possible to precisely determine a degree of damage to hair by employing simple chemical and image-analytical methods, which for example can be performed with use of a mobile data processing device (for example a smartphone), a few further simple devices (for example a UV LED), and a method based on predictive analytics. This can enable a targeted selection of products, for example cosmetic products, and/or may make it possible to provide personalised cosmetic products, for example hair cosmetics.

In various exemplary embodiments the method for determining a degree of damage to hair can be used in a method for selecting suitable cosmetic products, i.e. cosmetic products suitable for attaining a desired effect. The suitable products, in accordance with various exemplary embodiments, can also include personalised (what are known as "mass-customised") cosmetics.

In various exemplary embodiments an intensity of fluorescence light can be easily detected with the aid of image-analytical methods under standardised conditions. By use of mathematical models from the field of predictive analytics, a mathematical model can be created by measurement of standard hair samples which have a cysteic acid content determined on the basis of known complex methods, which mathematical model then allows a calculation of a content of cysteic acid and thus of hair damage in a hair sample, also referred to as a braid, from the consumer on the basis of the detected fluorescence light and fluorescence intensity determined on this basis. The image analysis can be performed here for example by employing known smartphones, tablets, or the like (with suitable apps).

In various exemplary embodiments the use of the mathematical model from the fields of predictive analytics (such as tree ensembles, neuronal networks or support vector machines) allows a much more precise calculation of the damage (which in the models forms a dependent variable) than would be possible with simple models, for example a simple linear regression. The methods can utilise a plurality of input variables in parallel, and also can display non-linear relationships. In various exemplary embodiments these models for example make it possible to integrate categorical, non-metric input variables, such as hair colour (for example blonde, brown, black, etc.) and/or ethnic affiliation of a hair type (for example Caucasian, Asian, Afro-American), which can have an influence on a resultant fluorescence intensity.

The hair colour can alternatively also be included in the model as a metric variable.

In various exemplary embodiments a method for determining a degree of damage to hair is provided. The method can comprise the following steps: whilst exposing a hair sample of the hair to UV light, detecting fluorescence light which is emitted by the hair sample, determining the fluorescence intensity on the basis of the detected light, and determining the degree of damage to the hair using said fluorescence intensity of the hair sample.

In various exemplary embodiments a method for determining a degree of damage to hair is provided. The method can comprise: wetting a hair sample, removed from the hair, with a fluorescence dye solution; removing fluorescence dye solution not adsorbed in the hair sample; whilst exposing the hair to UV light, detecting light which is emitted by fluorescence dye adsorbed in the hair sample; determining the fluorescence intensity on the basis of the detected light; and determining the degree of damage to the hair using said fluorescence intensity of the hair sample.

In other words, in various exemplary embodiments the inherent fluorescence of the damaged hair, the fluorescence of fluorescence dyes additionally introduced into the hair sample, or both, is/are used in a method for determining the degree of damage to hair.

In accordance with various embodiments, determining the degree of damage can comprise determining a relationship between a plurality of fluorescence intensity-influencing parameters and the fluorescence intensity by employing predictive analytics.

In accordance with various embodiments the plurality of fluorescence intensity-influencing parameters may include a hair colour and/or an ethnic affiliation of the hair type.

In accordance with various embodiments the predictive analytics can utilise at least one method from a group of methods, wherein the group of methods comprises:

linear or multi-linear regression, polynomial regression, neuronal network methods, support vector machine methods, decision tree methods (decision trees, random forest, tree ensembles), and further methods.

In accordance with various embodiments the detection of light may comprise producing a photo.

In accordance with various embodiments the detection of light may comprise directly detecting fluorescence light.

In accordance with various embodiments the detection of light may comprise the steps of determining a fluorescence intensity and/or determining the degree of damage to the hair by employing a mobile data processing apparatus.

In accordance with various embodiments the fluorescence dye solution may comprise rhodamine B, coumarin and/or fluorescein.

In accordance with various embodiments a wetting of the hair with the fluorescence dye solution can be spared, and instead of determining the fluorescence dyes absorbed by the damaged hair from the fluorescence dye solution, the inherent fluorescence of the damaged hair may be determined.

In accordance with various embodiments the UV light may have a wavelength in the range of from approximately 315 nm to approximately 380 nm.

In accordance with various embodiments the wetting of hair with a fluorescence dye solution may comprise the wetting of the hair sample for a predetermined period of time.

In accordance with various embodiments the method may further comprise: before detecting the light, generating defined conditions for the exposure of the hair sample to UV light and for the detection of light.

In accordance with various embodiments results from comparison measurements may be used in order to determine the degree of damage to the hair.

In various exemplary embodiments a device for determining a degree of damage to hair is provided. The device may comprise a UV lamp for exposing a hair sample to UV light, a device for detecting fluorescence light which is emitted by the hair sample, and a data processing device for determining the fluorescence intensity on the basis of the detected light and for determining the degree of damage of the hair using said fluorescence intensity. The fluorescence light may be an inherent fluorescence of the damaged hair and/or a fluorescence of fluorescence dye adsorbed in the hair sample. The hair sample can be removed from a head of hair, for example in order to wet the hair with a fluorescence dye solution and/or in order to detect the fluorescence light, or the hair sample can remain on a head, for example when detecting the inherent fluorescence of the hair.

In various exemplary embodiments a method for determining a user-specific hair treatment product is provided. The method can comprise the steps of determining the degree of damage to the hair of a user in accordance with various exemplary embodiments, determining, in a computer-assisted manner, treatment results that are attainable by employing a plurality of hair treatment products by employing predictive analytics using said determined degree of damage, and selecting the user-specific product on the basis of the determined treatment results.

In accordance with various embodiments the user-specific hair treatment product comprises a haircare product, a hair colorant product, a bleaching product, or a styling product (for example for hair smoothing or permanent waving).

Exemplary embodiments of the present disclosure are illustrated in the drawings and will be explained in greater detail hereinafter.

Figure 1A:
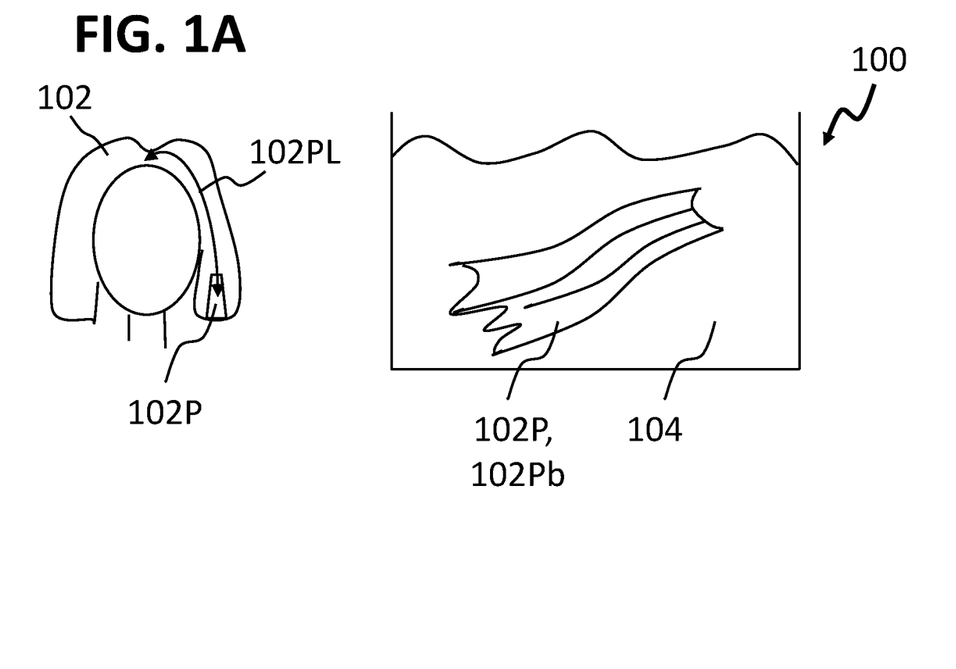
FIGS. 1A and 1B show a schematic depiction of a method for determining a degree of damage to hair in accordance with various exemplary embodiments, wherein in FIG. 1B a device for determining a degree of damage to hair in accordance with various exemplary embodiments is used.
Figure 1B:
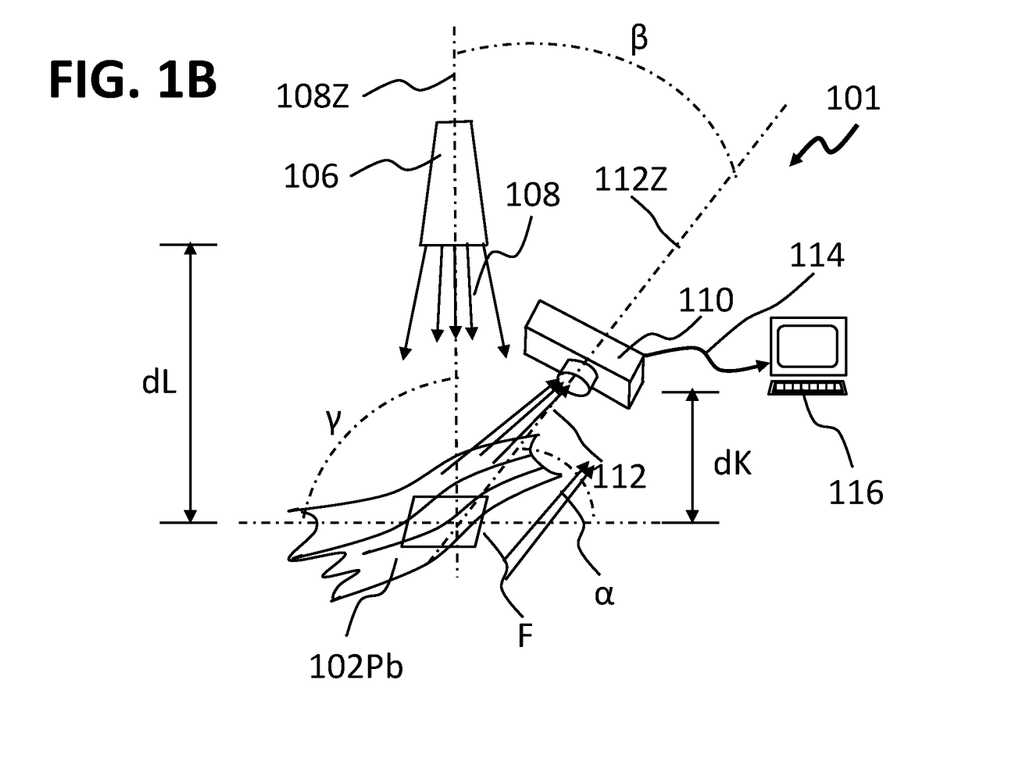

FIGS. 1A and 1B, in views 100, 101, show a schematic depiction of a method for determining a degree of damage to hair in accordance with various exemplary embodiments.

In accordance with various exemplary embodiments a hair sample 102P may be taken in order to determine a degree of damage to hair 102 of a user. The hair sample 102P may be taken for example in a removal 102PL from a scalp of hair of the user. The hair sample 102P can comprise a minimum amount of hair, which for example can be expressed as a minimal area which can be covered comprehensively by the hair sample 102P (for example spread out flat), for example at least about 1 $cm^2$, or for example as a minimum weight, for example at least about 0.5 g.

In accordance with various exemplary embodiments a degree of damage to hair 102 of a user may also be determined without removing a hair sample 102P. Fluorescence light 112 of the hair sample 102P may be detected for example on the head of the user, for example when detecting inherent fluorescence of the damaged hair 102, and/or in a case in which it is possible to wet the hair sample 102P on the head with a fluorescence dye solution 104.

In various exemplary embodiments the hair sample 102P may be wetted with a fluorescence dye solution 104, for example by being dipped into the fluorescence dye solution 104. The fluorescence dye solution 104 may comprise fluorescence dye, for example rhodamine B, coumarin and/or fluorescein, and/or another fluorescence dye, which similarly to the aforesaid fluorescence dyes has the property of being adsorbed to a greater extent by damaged hair, dissolved in a solvent, for example water. The fluorescence dye has the known property of being excited when exposed to UV light 108 and emitting longer-wave light 112 as a result of the excitation. The emitted light 112 is also referred to as fluorescence light 112.

The fluorescence dye solution 104 can be heavily diluted. The concentration of the fluorescence dye in the fluorescence dye solution 104 in various exemplary embodiments can be in a range of from approximately 0.01% (by weight) to approximately 0.1% (by weight), for example from approximately 0.01% to approximately 0.07%. The concentration of rhodamine B and the fluorescence dye solution 104 can be for example approximately 0.05% (by weight). The concentration of fluorescein in the fluorescence dye solution 104 can be for example approximately 0.04% (by weight). The concentration of coumarin in the fluorescence dye solution 104 can be for example approximately 0.02% (by weight).

The hair sample 102P can be wetted with the fluorescence dye solution 104 in various exemplary embodiments for a predetermined period of time, for example one second, ten seconds, one minute, five minutes, ten minutes, or any other suitable predetermined period of time, or for example for a minimum period of time, for example at least one second, ten seconds, one minute, five minutes, ten minutes, or any other suitable predetermined minimum period of time. During the wetting of the hair sample 102P with the fluorescence dye solution 104, the fluorescence dye can be at least partially adsorbed by the hair sample 102P, in particular by damaged hairs in the hair sample 102P. The wetted hair sample 102P is denoted as 102Pb.

In various exemplary embodiments, excess fluorescence dye solution 104, i.e. not adsorbed by the hair sample 102Pb, can be removed following the wetting of the hair sample 102P. The hair sample 102Pb for example can be rinsed, for example using water or, if the fluorescence dye solution 104 contains a solvent other than water, for example using this solvent. Generally, any method which is suitable for removing the excess fluorescence dye solution 104 and leaving the adsorbed fluorescence dye in the hair sample 102P without further damaging or modifying the hair sample 102Pb can be used. An incorrect measurement of the fluorescence intensity of the hair sample 102Pb can be avoided by the removal of the excess fluorescence dye solution 104.

Once the excess fluorescence dye solution 104 has been removed, the fluorescence intensity of the hair sample 102Pb can be determined.

In various exemplary embodiments a device for determining the degree of damage to the hair 102 in accordance with various exemplary embodiments can be used for this purpose, as is depicted schematically by way of example in a view 101 in FIG. 1B.

In various exemplary embodiments the hair sample 102Pb can be spread out so as to cover an area.

In various exemplary embodiments the hair sample 102Pb can be illuminated with UV light 108. The UV light can have a wavelength in a range of from approximately 315 nm to approximately 380 nm, for example in a range of from approximately 350 nm to approximately 375 nm, for example approximately 370 nm. In various exemplary embodiments UV light with a wavelength of less than about 315 nm can be used.

In various exemplary embodiments a light source 106 of the UV light 108 can be a UV lamp or a UV LED, for example. Generally, however, any light source which generates UV light 108 in the aforesaid wavelength range in an intensity sufficient for a standardised measurement of a fluorescence intensity as described below can be used. For example, a conventional UV lamp as used for example for checking the authenticity of banknotes can be used as light source 106.

In various exemplary embodiments the light source 106 can be arranged at a distance dL from the hair sample 102Pb, and can illuminate the hair sample at an angle γ, wherein the angle γ can be measured between a plane in which the hair sample 102Pb is spread out flat and a central beam 108Z of the UV light, which in various exemplary embodiments can be coincident with an optical axis of the light source 106.

In various exemplary embodiments the light source 106 can have a predetermined intensity of emitted light.

In various exemplary embodiments the intensity of emitted light, the angle γ, and the distance dL can be such that a region F of the hair sample 102Pb is exposed with a predetermined intensity of exposure, for example a predetermined minimum intensity of exposure.

In various exemplary embodiments, whilst the hair sample 102Pb is being exposed to the UV light 108, it is possible to detect light 112 (fluorescence light 112) which is emitted by fluorescence dye adsorbed in the hair sample 102Pb.

In various exemplary embodiments a device 110 for detecting the light 112 emitted by fluorescence dye adsorbed in the hair sample may be used to detect the light 112.

The device 110 for detecting the light 112 may be arranged at a distance dK from the hair sample 102Pb and may detect the light of the hair sample 102Pb at an angle α, wherein the angle α may be measured between a plane in which the hair sample 102Pb is spread out flat and a central beam 112Z of the detected light 112, which in various exemplary embodiments can be coincident with an optical axis of the device 110 for detecting the light 112.

The device 110 for detecting the light 112 and the light source 106 can be arranged at an angle β to one another. The angle β can be measured between the central beam 112Z of the detected light 112 and the central beam 108Z of the UV light.

The device 110 for detecting the light 112 by way of example can comprise a camera, for example a digital camera. The detection can comprise a step of generating a photo, for example a digital photo. The digital camera for example may be part of a smartphone, tablet, or a laptop, i.e. a mobile data processing device. Generally, however, any device 110 which allows an association of received intensity and detected information regarding the received intensity can be used to detect the light 112, for example an analogue camera, the recorded image of which may then be further processed quantitatively in respect of the detected intensity.

In various exemplary embodiments the distance dK and the angle α can be such that light in a predetermined area, for example the area F, is detected by the device 110 for detecting the light 112. For example, the aforesaid parameters can be coordinated such that the predetermined area has a predetermined size, for example a minimum or a maximum size, for example an area of at least about 1 cm$^2$, for example an area of at most about 10 cm$^2$.

In accordance with various exemplary embodiments the distances dL and dK and the angles α, β and γ and spatial positions (not shown) of the light source 106, the hair sample 106Pb and the device 110 for detecting the light 112) may be coordinated such that, in the case of a predefined hair sample 102Pb, as much light 112 as possible can be detected in the device 110 for detecting the light 112.

In various exemplary embodiments the aforesaid parameters can be coordinated such that they can be easily realised by a user, for example in the private field or in the services field.

In various exemplary embodiments the aforesaid parameters can be coordinated such that they correspond to the parameters used in reference measurements taken on standardised hair samples.

For a further standardisation, in various exemplary embodiments (not shown), light of a reference sample, for example of a material saturated with fluorescence dye solution and of known absorbency for the fluorescence dye, can be detected by the device 110 for detecting the light 112, at the same time as the hair sample 102Pb or successively.

In various exemplary embodiments the method for determining a degree of damage to hair may also comprise a step of determining a fluorescence intensity on the basis of the detected light 112.

In various exemplary embodiments the detected light 112 to this end may be transferred in processed form, for example in the form of a digital photo or another quantification of the detected light, to a data processing device 116. This is exemplified by the reference sign 114. The transfer can be implemented in a known manner, for example by employing a data cable, wireless data transfer (for example Wlan, ZigBee, Thread, Bluetooth or Near Field Communication (NFC)), or the transfer can be performed within a device if the device 110 for recording the light 112, as described above, is part of a data processing device (for example mobile telephone, tablet, laptop) which can also perform a function of the data processing device 116.

In order to receive and further process the data, the data processing device can be equipped for example with appropriate software, for example an app.

In various exemplary embodiments a measured value for the detected light 112, for example a number of counts (counted measurand) in a predetermined image region or the like, can firstly be determined by employing image-analytical methods on the basis of the detected light 112, which for example was detected under standardised conditions, for example by employing a predetermination inter alia of the above-mentioned parameters.

In various exemplary embodiments a fluorescence intensity can be determined on the basis of the determined measured value for the detected light 112. Mathematical models from the field of predictive analytics can be used for this purpose in order to determine a relationship between the measured value for the detected light 112 and an associated standardised fluorescence intensity, for example under consideration of further parameters, such as a luminous intensity of the light source 106, the above-mentioned distances and angles, and aperture of the device 110 for detecting the light 112, and further influencing variables which may influence a ratio of fluorescence intensity and detected light.

In various exemplary embodiments the light detected by the reference sample may be included in the determination of the measured value.

In various exemplary embodiments a cysteic acid content can be determined on the basis of the determined fluorescence intensity. For this purpose, mathematical models from the field of predictive analytics can again be used, this time in order to determine a relationship between the (standardised) fluorescence intensity and an associated cysteic acid content (and therefore a degree of damage of the hair sample 102Pb).

In various exemplary embodiments a relationship for example between cysteic acid content and fluorescence intensity or corresponding data values, for example in the form of associated data pairs, which were determined or mathematically modelled by employing measurement of standard hair samples having a cysteic acid content determined on the basis of known complex methods, can be included as independent parameter in the model.

Figure 2:
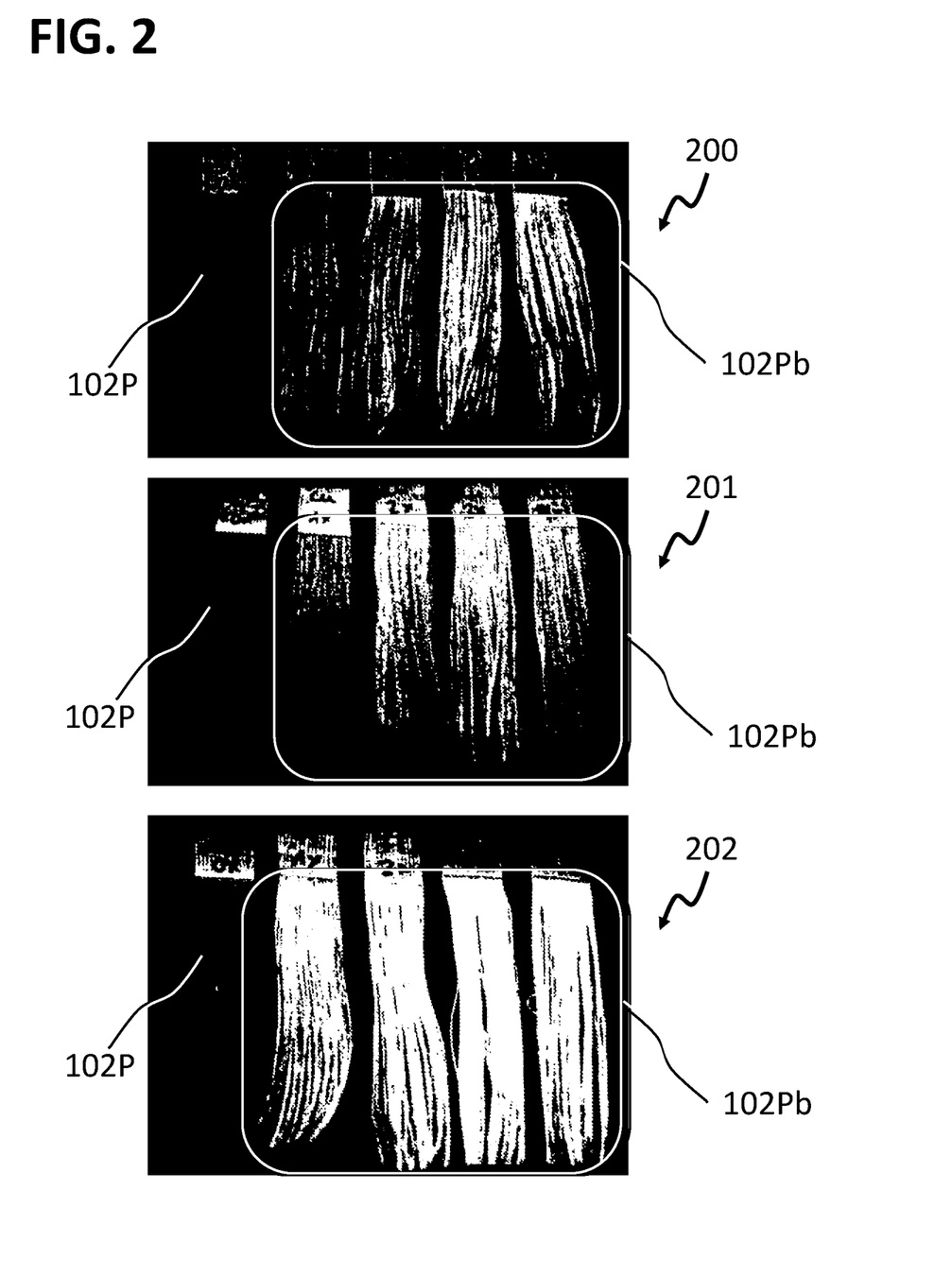
FIG. 2 shows images of the fluorescence of various fluorescence dyes (and inherent fluorescence as applicable) of hair samples with different degrees of damage in accordance with various exemplary embodiments.

FIG. 2 shows images 200, 201, 202 of the fluorescence of various fluorescence dyes of standard hair samples with different degrees of damage in accordance with various exemplary embodiments.

Here, in each case the left hair samples 102P are untreated (ultra-bleached Ox), and those hair samples 102Pb arranged to the right are wetted with a fluorescence dye solution. The fluorescence dyes used here were rhodamine B, coumarin and fluorescein (from top to bottom).

The shown wetted hair samples 102Pb were damaged to differing degrees, more specifically (in each case from left to right) by ultra-bleaching once, twice, three times or four times.

A fluorescence intensity increasing in each case from left to right is visible on the basis of the photos. These and further or similar standard samples can be used to establish the relationship between cysteic acid content and fluorescence intensity or corresponding data values used to determine the degree of damage to a new hair sample 102P (these and possibly further data are denoted in FIG. 3 by 302).

Figure 3:
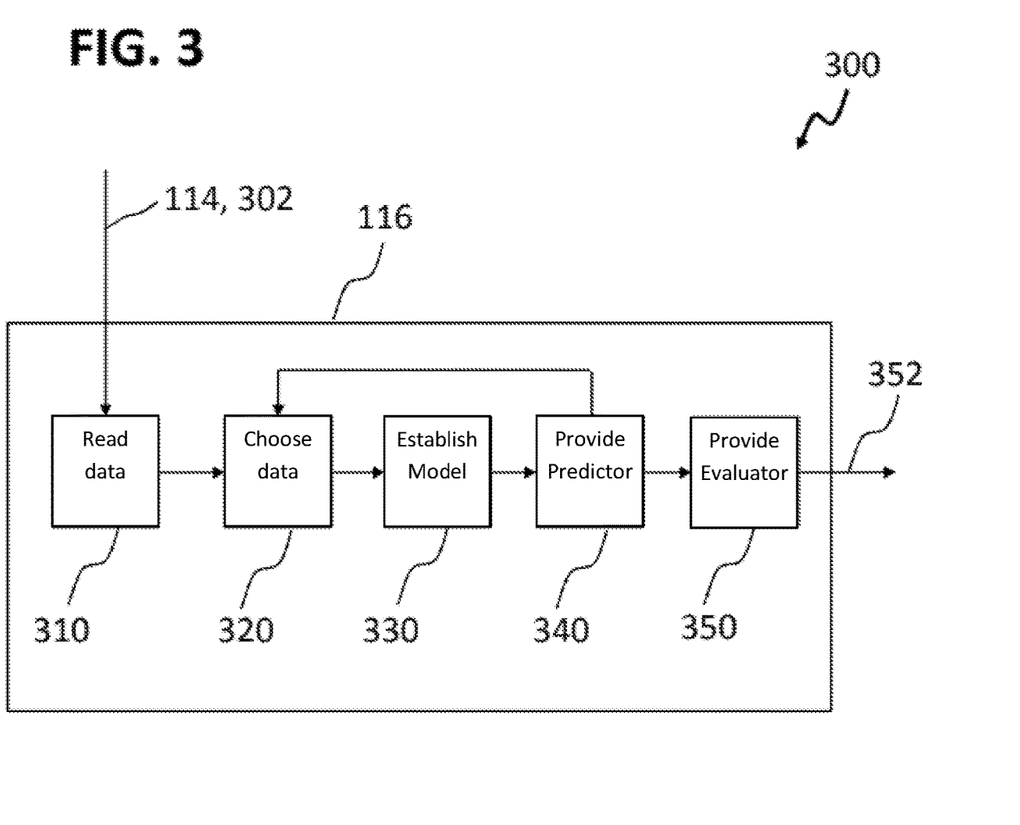
FIG. 3 shows a schematic depiction of a use of determined fluorescence intensities in a method for determining a degree of damage to hair in accordance with various exemplary embodiments.

FIG. 3 shows a schematic depiction 300 of a use of determined fluorescence intensities and a method for determining a degree of damage to hair in accordance with various exemplary embodiments.

A continuous model of fluorescence intensity and the degree of damage can be generated by employing predictive analytics in various exemplary embodiments, such that it is possible, for a value of a fluorescence intensity or a combination of fluorescence intensity with further parameters influencing an association of fluorescence intensity and degree of damage, to determine a value for the degree of damage, also with the aid of the model, if the input combination of data does not correspond to any of the corresponding experimental values or value combinations.

In various exemplary embodiments the degree of damage can be determined in a categorical scale (for example slight, medium, severe).

In various exemplary embodiments the degree of damage can be determined in a metric scale (for example percentage of the content of cysteic acid).

In various exemplary embodiments the further parameters, which for example can result in a different adsorption of fluorescence dye with the same degree of damage, can comprise for example a hair colour (for example blonde, brown, black, etc.) and/or an ethnic affiliation of the hair type (for example Caucasian, Asian, Afro-American).

Predictive analytics can be described generally as a method for extracting information from large data volumes and generating a model on the basis of this data, which model makes it possible to make predictions also for values which are not part of the dataset. When applying a method based on predictive analytics, some of the dataset can typically be used as a training dataset (also referred to as a training set or training data). This training dataset can then be used to generate one or more models which can then be tested on the basis of the data not part of the training dataset, on the basis of the data as a whole, or on the basis of a specially selected part of the data.

For an assessment of the model, i.e. a determination of the goodness of fit, a coefficient of determination $R^2$, a mean absolute error, a mean squared error, a standard deviation and/or a mean deviation can be used, for example.

The coefficient of determination $R^2$ can correspond to a squared correlation coefficient for a linear regression model. For another model (another relationship), it can be defined differently.

In accordance with various exemplary embodiments, various functions or methods can be used for the modelling by employing predictive analytics. In a simple case, a multiple linear regression can be used for example. Improved results can be attained typically with use of polynomial regressions, neuronal networks, support vector machines, decision trees (for example tree ensembles), or the like.

In various exemplary embodiments the described method for computer-assisted prediction of properties of hair colours can be carried out by employing a data processing device 116.

The data processing device, as described above in conjunction with FIG. 1B, can comprise for example a mobile data processing device, for example a smart phone, a tablet or a laptop, but also another computer, or any other data processing device suitable for storing and providing the data and carrying out the method based on predictive analytics, that is to say for example any data processing device, for example a smart mirror, with a sufficiently large data memory and sufficiently powerful processor.

In various exemplary embodiments the data processing device can comprise at least one input device for inputting information into the data processing device, for example for inputting the hair colour data and as appropriate for inputting instructions, parameters, etc. for carrying out the method. The input device may comprise for example a keypad, a touch-sensitive screen, or a microphone.

In various exemplary embodiments the data processing device can comprise at least one output device for outputting information, for example for outputting results.

In various exemplary embodiments the at least one output device can comprise a screen and/or a printer and/or loudspeaker.

In various exemplary embodiments, any program (for example an app) which provides a functionality of this kind can be used for a modelling by employing predictive analytics.

The components 310, 320, 330, 340, 350 shown in FIG. 3 can represent individual processes performed during the execution of the method based on predictive analytics.

In various exemplary embodiments the determined fluorescence intensity values 114 and further parameters 302, which for example comprise the data pairs of the reference measurements, and possibly further parameters can be read in at 310 by the predictive analytics program (for example software, for example an app).

In various exemplary embodiments filters can be provided at 320 which choose the data that is to be used to determine the degree of damage, as appropriate from the totality of data provided at 310.

In 330 a functional component for establishing a model, for example for performing a simple linear regression for the data selected at 320, may be provided in accordance with various exemplary embodiments.

A relationship between the plurality of input parameters, which comprise the fluorescence intensity and possibly further parameters, and the degree of damage can be determined by employing the model, for example the regression. This determined relationship can also be referred to as a model. A principle for adapting the model to the data can be an optimisation of the smallest squared error. In other words, an error can be minimised by employing the smallest square method.

In various exemplary embodiments a predictor can be provided at 340, to which both the results of the model, for example the simple linear regression, and possibly unused (non-selected) hair colour data from 320, can be fed. With use of the previously determined relationship, the predictor can determine values for the degree of damage for all selected colour precondition parameters.

In various exemplary embodiments an evaluator can be provided at 350, which evaluator, with use of the values for the modelled degree of damage determined by employing the predictor and with use of the degree of damage actually measured (for reference data 203), calculates values which can be used as a measure for a goodness of fit of the model. For example, a coefficient of determination $R^2$ (which for a linear regression corresponds to a squared correlation coefficient; generally, good values for the coefficient of determination $R^2$ can lie for example between from about 0.8 and about 1.0), a mean absolute error, a mean squared error, a standard deviation and/or a mean absolute deviation can be determined. Particular attention can be focused in various exemplary embodiments on the coefficient of determination $R^2$ and on the mean absolute deviation.

In various exemplary embodiments the result of the determination of the degree of damage to the hair can be output, for example displayed, at 352.

In various exemplary embodiments, when determining the degree of damage of the hair 102, the removal 102PL (see FIG. 1A) sustained by the hair sample 102P when removed from the scalp of the user may also be included. Typically, at least in the case of longer hair, the hair 102 is damaged to a greater extent at the hair ends than in the vicinity of the scalp. Accordingly, a mean damage of the hair or for example a maximum damage of the hair can be determined on the basis of the removal 102PL and a total length of the hair 102, for example by employing the model.

In various exemplary embodiments, instead of the method based on predictive analytics, other methods, for example simpler methods, for associating the degree of damage with the specific fluorescence intensity can be used.

Figure 4:
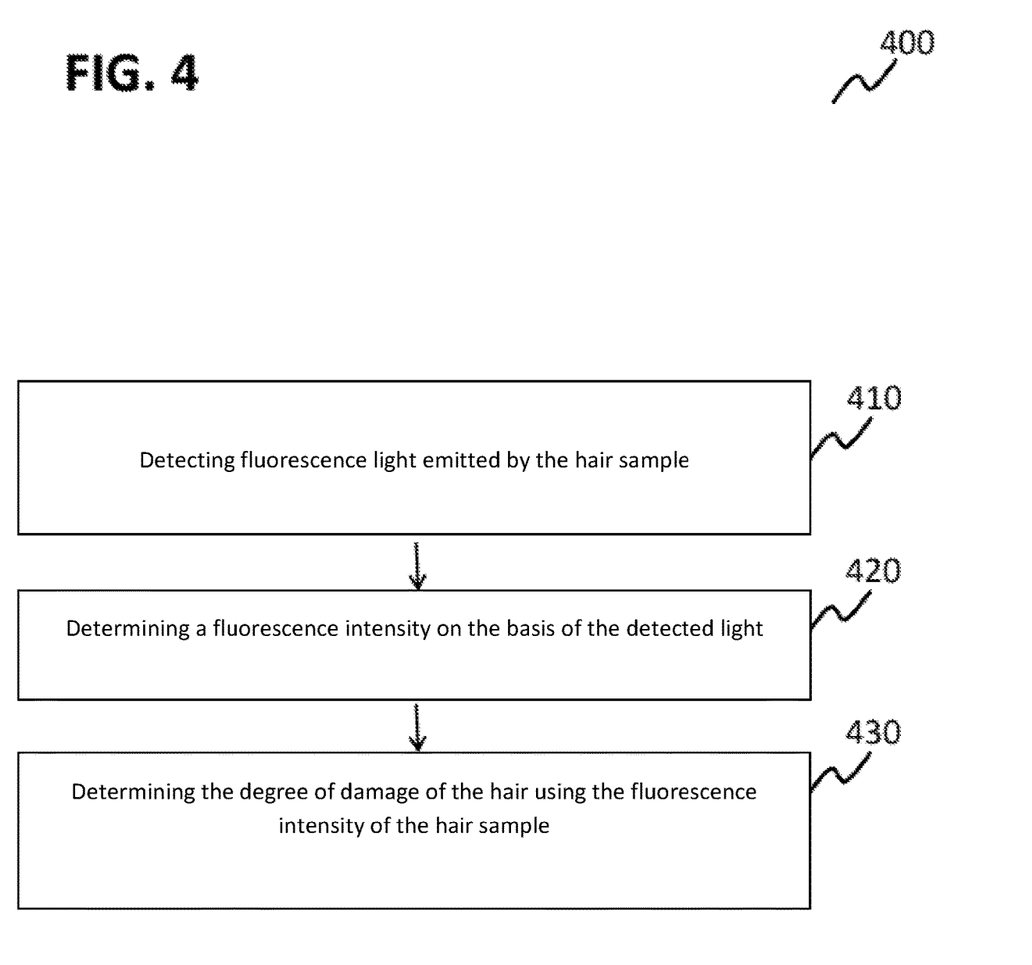
FIG. 4 shows a flow diagram depicting a method for determining a degree of damage to hair in accordance with various exemplary embodiments.

FIG. 4 shows a flow diagram 400 which depicts a method for determining a degree of damage of hair in accordance with various exemplary embodiments.

In various exemplary embodiments the, whilst a hair sample is exposed to UV light, the method may also comprise the steps of detecting fluorescence light emitted by the hair sample (at 410), determining a fluorescence intensity on the basis of the detected light (at 420) and determining the degree of damage of the hair using the fluorescence intensity of the hair sample (at 430). The fluorescence light for example can be an inherent fluorescence of the damaged hair.

Figure 5:
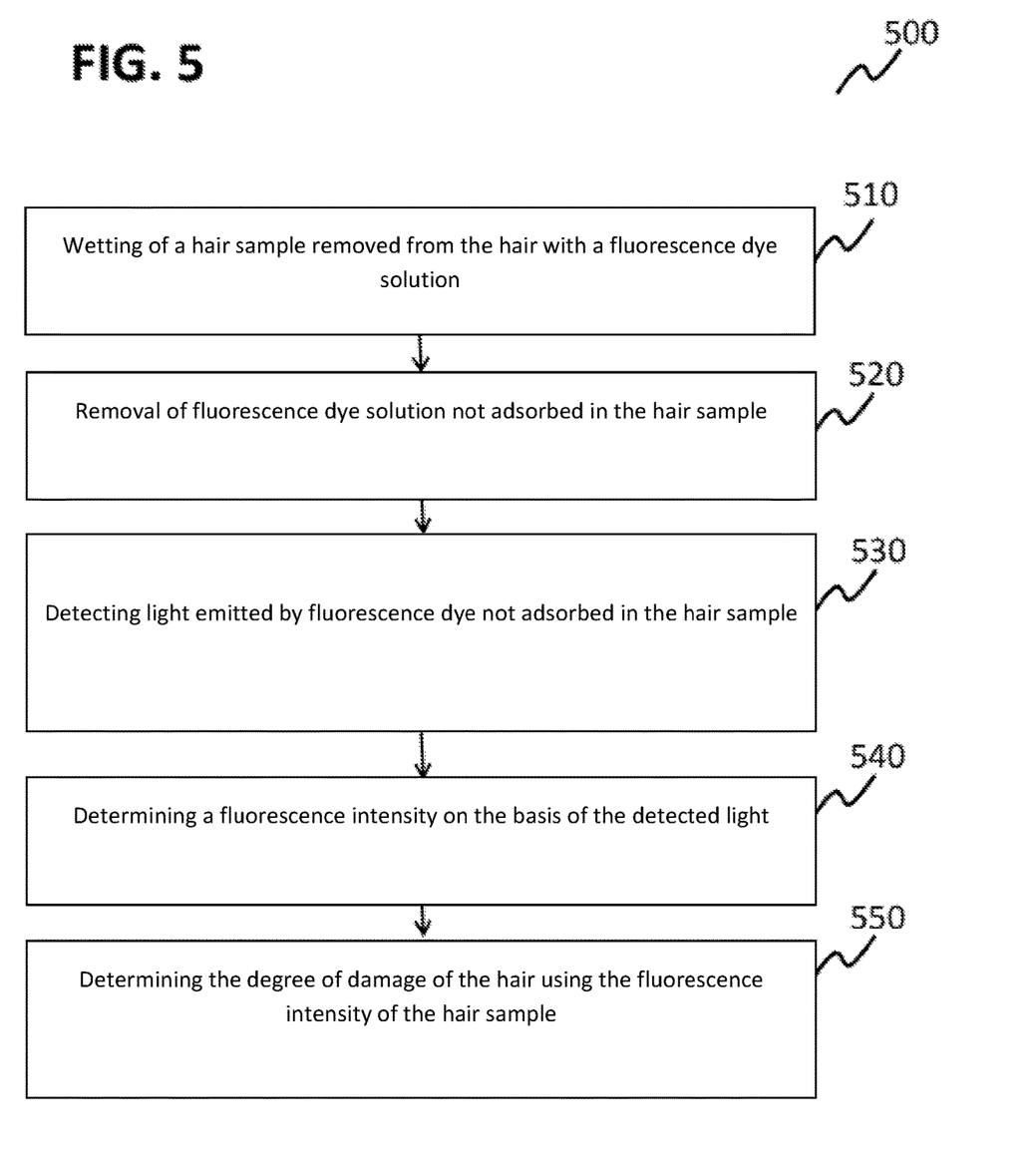
FIG. 5 shows a flow diagram depicting a method for determining a degree of damage to hair in accordance with various exemplary embodiments.

FIG. 5 shows a flow diagram 500 depicting a method for determining a degree of damage of hair in accordance with various exemplary embodiments.

In various exemplary embodiments the method can comprise a wetting of a hair sample removed from the hair with a fluorescence dye solution (at 510), a removal of fluorescence dye solution not adsorbed in the hair sample (at 520), whilst the hair sample is being exposed with UV light, detecting light emitted by fluorescence dye not adsorbed in the hair sample (at 530), determining a fluorescence intensity on the basis of the detected light (at 540), and determining the degree of damage of the hair using the fluorescence intensity of the hair sample (at 550).

Figure 6:
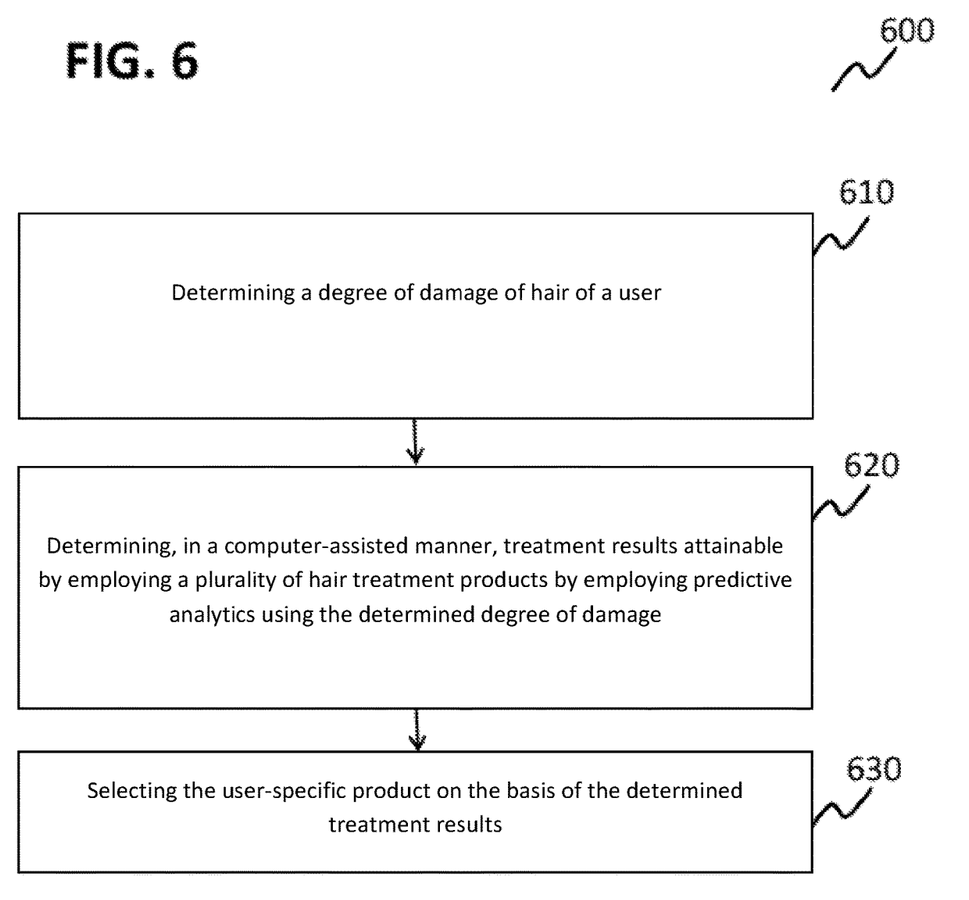
FIG. 6 shows a flow diagram depicting a method for determining a user-specific hair treatment product in accordance with various exemplary embodiments.

FIG. 6 shows a flow diagram 600 depicting a method for determining a user-specific hair treatment product in accordance with various exemplary embodiments.

In various exemplary embodiments the above-described method for determining a degree of damage of hair or the above-described device for determining a degree of damage of hair can be used for a method for determining a user-specific hair treatment product.

In various exemplary embodiments the method for determining a user-specific hair treatment product may comprise: determining a degree of damage of hair of a user in accordance with one of the above-described exemplary embodiments (at 610), determining, in a computer-assisted manner, treatment results that are attainable by employing a plurality of hair treatment products by employing predictive analytics using said determined degree of damage (at 620), and selecting the user-specific product on the basis of the determined treatment results (at 630).

In various exemplary embodiments the user-specific hair treatment product may comprise a haircare product, a hair colorant product, a bleaching product, or a styling product, for example a smoothing agent, such as a straightener or relaxer or a product for permanent waving.

In various exemplary embodiments the method for determining a user-specific hair treatment product may also comprise the initiation of an ordering process, preferably by loading a website of a manufacturer of individual hair care products, in particular individual hair colorant products, individual bleaching products or an individual styling product.

Customers are always looking for a product tailored individually to their requirements. This may be a product produced especially for the customer or what is known as a "mass customised" product. In the case of a "mass customised" product, individualisation can be achieved. These "mass customised" products are preferably based on the concept of modularisation, that is to say the product can be compiled in a tailored manner from various modules/building blocks.

There are often numerous dependencies between the many different features/ingredients of a product, and these can be expressed as "imperatives" or "prohibitions". In order to obtain a clear product definition, it can be advantageous that the ordering process is performed with the aid of a product configurator. This configurator helps the customer in their selection of the features/ingredients and indicates to the customer the reliable/unreliable combinations of features, wherein the latter cannot be selected.

In the case of haircare products, hair colorant products, bleaching products or styling products, the relevant product features in particular comprise the chemical ingredients of the products, the physical properties of the products, and the formulation of the products. With the aid of a product configurator, the selection of chemically and/or physically incompatible ingredients or the selection of ingredients unsuitable for the determined degree of damage can be avoided, for example. Conversely, the selection for ingredients suitable for the determined degree of damage can be stipulated or proposed by the product configurator.

In various exemplary embodiments, a visit to a hairdresser may be recommended in the case of certain degrees of hair damage. In various exemplary embodiments a booking process can be initiated directly via the software/app that determines the degree of damage. To this end, for example the contact information of hairdressers can be stored in the software/app and this information can be displayed to the user. In addition, the selection can be limited by filters, such as postcode. Alternatively, a hairdresser appointment can be booked via a separate software/app, such as Treatwell.

While at least one exemplary embodiment has been presented in the foregoing detailed description, it should be appreciated that a vast number of variations exist. It should also be appreciated that the exemplary embodiment or exemplary embodiments are only examples, and are not intended to limit the scope, applicability, or configuration of the various embodiments in any way. Rather, the foregoing detailed description will provide those skilled in the art with a convenient road map for implementing an exemplary embodiment as contemplated herein. It being understood that various changes may be made in the function and arrangement of elements described in an exemplary embodiment without departing from the scope of the various embodiments as set forth in the appended claims.

The invention claimed is:

1. A method for determining a degree of damage to hair, the method comprising the steps of:
  creating a model by exposing to UV light hair specimens having predetermined cysteic acid contents and establishing a relationship between fluorescence intensity and cysteic acid content;
  exposing a hair sample of the hair to UV light and detecting light emitted by the hair sample to define detected light;
  determining a fluorescence intensity on a basis of the detected light; and
  determining a degree of damage to the hair using the fluorescence intensity of the hair sample and the model to determine a content of cysteic acid in the hair.

2. The method according to claim 1, further comprising the steps of:
  wetting the hair sample with a fluorescence dye solution including a fluorescent dye; and
  removing the fluorescence dye solution not adsorbed in the hair sample,
  wherein the detected light includes light emitted at least in part by the fluorescence dye adsorbed in the hair sample.

3. The method according to claim 2, wherein the fluorescence dye solution further comprises rhodamine B, coumarin and/or fluorescein.

4. The method according to claim 2, wherein wetting the hair sample with a fluorescence dye solution comprises wetting the hair sample for a predetermined period of time.

5. The method according to claim 1, wherein the detected light comprises light emitted by the fluorescent dye adsorbed in the hair sample.

6. The method according to claim 1, wherein the detected light comprises light emitted by the fluorescent dye adsorbed in the hair sample, wherein the fluorescent dye comprises rhodamine B and coumarin, fluorescein, or coumarin and fluorescein.

7. The method according to claim 1, wherein determining the degree of damage comprises determining a relationship between a plurality of fluorescence intensity-influencing parameters and the fluorescence intensity by means of predictive analytics.

8. The method according to claim 7, wherein the plurality of fluorescence intensity-influencing parameters comprise a hair colour and/or an ethnic affiliation of a hair type.

9. The method according to claim 7, wherein the predictive analytics uses at least one method from a group of methods, wherein the group of methods comprises:
  linear or multi-linear regression,
  polynomial regression,
  neuronal network methods,
  support vector machine methods; and
  decision tree methods.

10. The method according to claim 7, wherein the plurality of fluorescence intensity-influencing parameters comprise a hair colour and an ethnic affiliation of a hair type.

11. The method according to claim 1, wherein detecting light comprises producing a photo or directly capturing light.

12. The method according to claim 1, wherein detecting light comprises:
  determining the fluorescence intensity and/or
  determining the degree of damage to the hair.

13. The method according to claim 1, wherein the UV light has a wavelength of from 315 nm to 380 nm.

14. The method according to claim 1, further comprising the step of:
  before detecting the light, generating defined conditions for exposure of the hair sample to UV light and for detection of light.

15. The method according to claim 1, wherein results from comparison measurements are used to determine the degree of damage to the hair.

16. A method for determining a user-specific hair treatment product, comprising the steps of:
  determining a degree of damage to the hair of a user in accordance with claim 1;
  determining, in a computer-assisted manner, treatment results that are attainable using a plurality of hair treatment products and predictive analytics using the determined degree of damage; and
  selecting the user-specific treatment product on a basis of the determined treatment results.

17. The method according to claim 16, wherein the user-specific hair treatment product comprises a haircare product or a hair colorant product, a bleaching product or a styling product.

18. The method according to claim 1, wherein the detected light is a light emitted by rhodamine B adsorbed in the hair sample.

19. A device for determining a degree of damage to hair, the device comprising:
- a UV lamp configured for exposing a hair sample of the hair to UV light;
- a device configured for detecting fluorescence light that is emitted by the hair sample to define detected light, wherein the detected light is an inherent fluorescence of the hair and/or is a light emitted by a fluorescent dye adsorbed in the hair sample, wherein the fluorescent dye comprises rhodamine B; and
- a mobile data processing device configured for determining a fluorescence intensity on a basis of the detected light and for determining a degree of damage of the hair using the fluorescence intensity, wherein the mobile data processing device contains or is in communication with a model including a relationship between fluorescence intensity and cysteic acid content of previously tested hair specimens.

20. The device according to claim 19, wherein the detected light comprises light emitted by the fluorescent dye adsorbed in the hair sample.

* * * * *